United States Patent
Zhu et al.

(10) Patent No.: US 7,041,661 B2
(45) Date of Patent: May 9, 2006

(54) USE OF THIAZOLOBENZOHETEROCYCLES FOR TREATING MULTIPLE SCLEROSIS

(75) Inventors: Bin Zhu, Bridgewater, NJ (US); Joseph Wettstein, Lebanon, NJ (US); Margaret A. Petty, Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 77 days.

(21) Appl. No.: 10/737,634

(22) Filed: Dec. 16, 2003

(65) Prior Publication Data

US 2004/0147504 A1 Jul. 29, 2004

Related U.S. Application Data

(60) Provisional application No. 60/434,003, filed on Dec. 17, 2002.

(51) Int. Cl.
*A61K 31/554* (2006.01)

(52) U.S. Cl. .............................. 514/211.09; 514/211.1; 514/211.11; 514/211.12

(58) Field of Classification Search ............ 514/211.09, 514/211.1, 211.11, 211.12, 211.01
See application file for complete search history.

(56) References Cited

U.S. PATENT DOCUMENTS

| 5,008,280 A | 4/1991 | Gueremy et al. |
| 6,369,221 B1 * | 4/2002 | Hardy et al. ................. 540/497 |

FOREIGN PATENT DOCUMENTS

| EP | 0374040 | 3/1993 |
| WO | WO99/05147 | 2/1999 |
| WO | WO02100880 | 12/2002 |

OTHER PUBLICATIONS

Gilgun–Sherki et al, Riluzole suppresses experimental autoimmune encephalomyelitis: implications for the treatment of multiple sclerosis, Brain Res., Vo. 989, No. 2, Nov., 2003, pp196–204.
Matute C, Characteristics of acute and chronic kainate excitotoxic damage to the optic nerve, Proceedings of the National Academy of Sciences of USA, National Academy of Science, Washington, U.S., vol. 95, No. 17, Aug. 1998, pp 10229–10234.
Matute et al, The link between excitotoxid oligodendroglial death and demyelinating diseases, Trends in Neuroscience, Apr. 2001, pp 224–230.
Adams, R. A. et al, Multiple Sclerosis and Allied Demyelinative Diseases, Principles of Neurology, 6th Edition, 1997, pp 902–927.
Bagetta G et al, Prevention by the NMDA receptor antagonist, MK801 of neuronal loss produced by tetanus toxin in the rat hippocampus, Br. J. Pharmacology, vol. 101, 1990, pp 776–780.
Dickenson A. H. et al, Antagonism at the glycine site on the NMDA receptor reduces spinal nociception in the rat, Neurosc. Letters vol. 121, 1991, pp 263–266.
Hauser S. L. et al, Multiple Sclerosis and Other Demyelinating Diseases, Harrison's Principles of Internal Medicine, 14th Edition, vol. 2, 1998, pp 1409–1419.
Kehne J. H. et al, NMDA receptor complex antagonists have potential anxiolytic effects as measured with separation–induced ultrasonic vocalizations, European Journal of Pharmacology, vol. 193, (1991), pp 283–292.
Lipton,S. A. et al, Synergistic Effects of HIV Coat Protein and NMDA Receptor—Mediated Neurotoxicity, Neuron, vol. 7, 1991, pp 111–118.
Mosinger J. L. et al, Blockade of Both NMDA and Non–NMDA Receptors is Required for Optimal Protection Against Ischemic Neuronal Degeneration in the Vivo Adult Mammalian Retina, Experimental Neurology, vol. 113, 1991, pp 10–17.
Pujol, R et al, Implication of non–NMDA and NMDA receptors in cochlear ischemia, Neuro Report, vol. 3, 1992, pp 200–302.
Reynolds Gavin P, Development in the drug treatment of schizophrenia, TIPS, vol. 13, 1992, pp 116–121.
Sluta K. A. et al, An experimental arthritis model in rats: the effects of NMDA and non–NMDA antagonists on aspartate and glutamate release in the dorsal horn, Neurosc. Letters, vol. 149, 1993, pp 99–102.
Sorrels T. L. et al, Induction of feeding by 7–chlorokynurenic acid, a strychnine–insensitive glycine binding site antagonist, Brain Research, vol. 572, 1992, pp 265–268.
Trullas R et al, Functional antagonists at the NMDA receptor complex exhibit antidepressant actions, European Journal of Pharmacology, vol. 185, 1990, pp 1–10.

* cited by examiner

Primary Examiner—Dwayne C. Jones
(74) Attorney, Agent, or Firm—Irving Newman

(57) ABSTRACT

The invention relates to the use of compound of Formula I in treating patients for inflammatory or neuropathic pain as well as various symptoms of multiple sclerosis

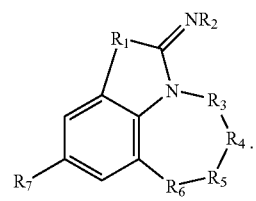

(I)

7 Claims, 2 Drawing Sheets

Figure 1: Effects of Compound A on neurological scores in SJL EAE mice (study 1)
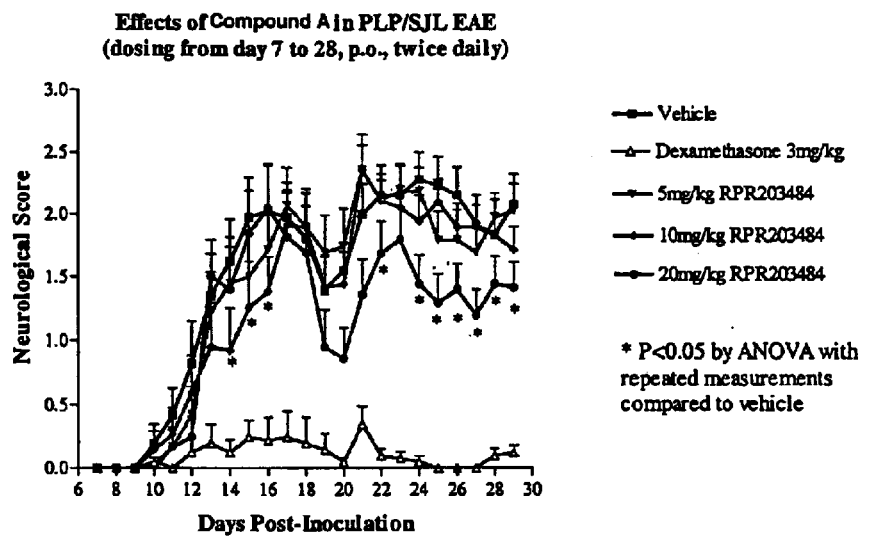
Figure 2: Effects of Compound A on neurological scores in SJL EAE mice (study 2)
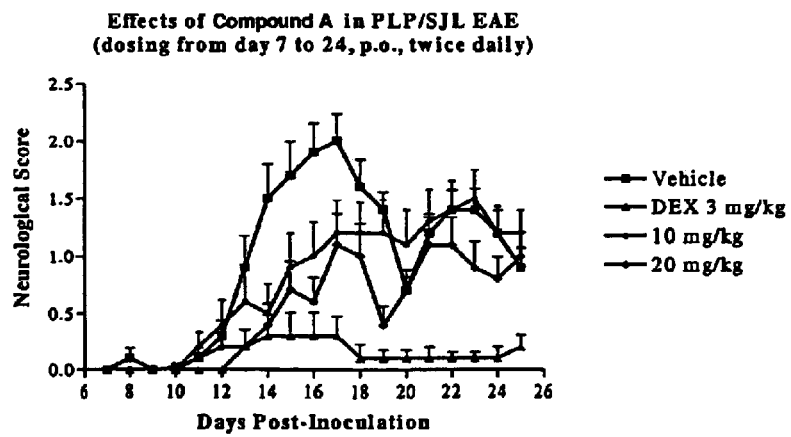

Figure 3: Effects of Compound A on neurological scores in DA rat EAE
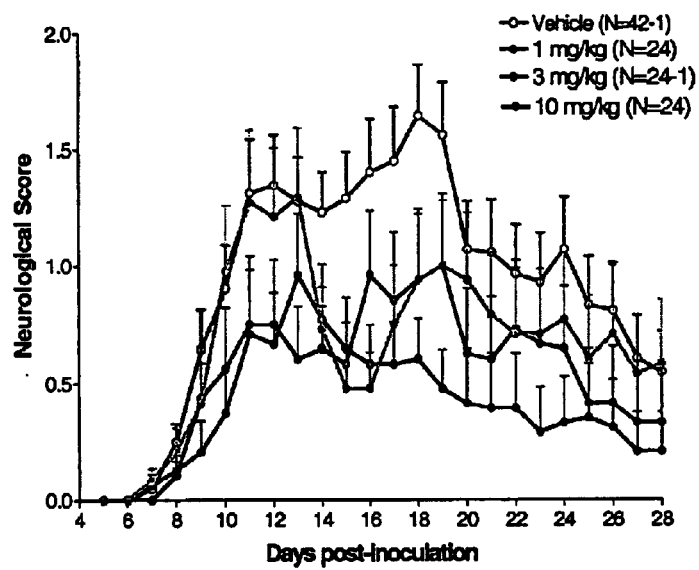
Figure 4: Effects of Compound B on neurological scores in DA rat EAE
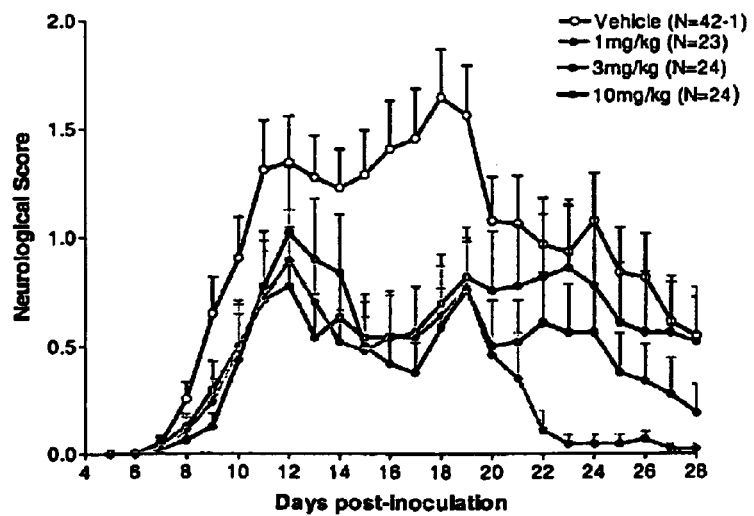

USE OF THIAZOLOBENZOHETEROCYCLES FOR TREATING MULTIPLE SCLEROSIS

CROSS REFERENCE TO RELATED APPLICATIONS

This application the benefit of U.S. Provisional Application No. 60/434,003, filed on 17 Dec. 2002.

FIELD OF THE INVENTION

The present invention relates to methods of treating multiple sclerosis. In particular, the present invention relates to the treatment of multiple sclerosis with the thiazolobenzoheterocyclic compounds of formula:

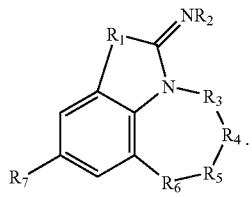

(I)

their isomers, racemates, enantiomers, their salts, and medicaments containing them.

BACKROUND OF THE INVENTION

Thiazolobenzoheterocyclic compounds of formula I are disclosed generically in U.S. Pat. No. 6,369,221, issued on Apr. 9, 2002, wherein it is disclosed that the compounds are anticonvulsants and interfere with glutamatergic transmission and are therefore useful for the treatment or prevention of all ischaemias (such as local or global ischaemia) following cerebrovascular accidents such as thromboembolic and haemorrhagic stroke, cardiac arrest, arterial hypotension, cardiac, vascular or pulmonary surgery or severe hypoglycaemia. They are also useful in the treatment of the effects caused by anoxia, whether it is perinatal or subsequent to drowning, high pressure or cerebrospinal lesions. These compounds may also be used to treat or prevent the development of neurodegenerative diseases, of HUNTINGDON's chorea, of ALZHEIMER's disease and other dementias, of amyotrophic lateral sclerosis or of other motor neuron diseases, of olivopontocerebellar atrophy and of PARKINSON's disease. These compounds may also be used against epileptogenic (epilepsy) and/or convulsive manifestations, for the treatment of cerebral or spinal traumas, of traumas linked to degeneration of the inner ear (R. PUJOL et al., Neuroreport, 3, 299–302 (1992)) or of the retina (J. L. MONSINGER et al., Exp. Neurol., 113, 10–17 (1991)), of tinnitus, of anxiety (KEHNE et al., Eur. J. Pharmacol., 193, 283 (1991)), of depression (TRULLAS et al., Eur. J. Pharmacol., 185, 1, (1990)), of schizophrenia (REYNOLDS, TIPS, 13, 116 (1992)), of TOURETTE's syndrome, of hepatic encephalopathies, of sleep disorders, of attention deficit disorders, of disorders of hormonal conditions (excess secretion of GH or LH, secretion of corticosterone), as analgesics (DICKENSON et al., Neurosc. Letters, 121, 263 (1991)), anti-inflammatory agents (SLUTA et al., Neurosc. Letters, 149, 99–102 (1993)), antianoretics (SORRELS et al., Brain Res., 572, 265 (1992)), antimigraine drugs, antiemetics and to treat poisoning by neurotoxins and other substances which are NMDA or AMPA receptor agonists, as well as neurological disorders associated with viral diseases such as viral meningitis and encephalitis, AIDS (LIPTON et al., Neuron 7, 111 (1991)), rabies, measles and tetanus (BAGETTA et al., Br. J. Pharmacol., 101, 776 (1990)). These compounds are also useful for the prevention of, tolerance to and dependency on the symptoms of withdrawal from drugs and alcohol, and of inhibition of addiction to and of dependency on opiates, barbiturates, amphetamine and benzodiazepines. They may also be used in the treatment of deficiencies linked to mitochrondrial abnormalities such as mitochrondrial myopathy, LEBER's syndrome, WERNICKE's encephalopathy, RETT's syndrome, homocysteinaemia, hyperprolinaemia, hydroxybutyric-aminoaciduria, saturnine encephalopathy (chronic lead poisoning) and sulphite oxidase deficiency.

The contents of the aforementioned patent are hereby incorporated herein by reference.

Multiple sclerosis (MS) is a debilitating, inflammatory, neurological illness characterized by demyelination of the central nervous system. The disease primarily affects young adults with a higher incidence in females. Symptoms of the disease include fatigue, numbness, tremor, tingling, dysesthesias, visual disturbances, dizziness, cognitive impairment, urological dysfunction, decreased mobility, and depression. Four types classify the clinical patterns of the disease: relapsing-remitting, secondary progressive, primary-progressive and progressive-relapsing (S. L. Hauser and D. E. Goodkin, Multiple Sclerosis and Other Demyelinating Diseases in Harrison's Principles of Internal Medicine $14^{th}$ Edition, vol. 2, Mc Graw-Hill, 1998, pp. 2409–2419).

The exact etiology of MS is unknown; however, it is strongly suspected that the demyelination characteristic of the disease is the result of an autoimmune response, perhaps triggered by an environmental insult, e.g. a viral infection. Specifically, it is hypothesized that MS is caused by a T-cell-mediated, autoimmune inflammatory reaction. The autoimmune basis is strongly supported by the fact that antibodies specific to myelin basic protein (MBP) have been found in the serum and cerebrospinal fluid of MS patients, and these antibodies, along with T-cells that are reactive to MBP and other myelin proteolipids, increase with disease activity. Furthermore, at the cellular, level it is speculated that T-cell proliferation and other cellular events, such as activation of B cells and macrophages and secretion of cytokines accompanied by a breakdown of the blood-brain barrier, can cause destruction of myelin and oligodendrocytes. (R. A. Adams, M. V. Victor and A. H. Ropper eds, Principles of Neurology, Mc Graw-Hill, New York, 1997, pp.903–921). Progressive MS (primary and secondary) may be based on a nuerodegenerative process occurring with demyelination.

At the present time, there is no cure for MS. Current therapies are aimed at alleviating the symptoms of the disease and arresting its progress, as much as possible. Depending upon the type, drug treatment usually entails the use of disease-modifying agents such as the interferons (interferon beta 1-a, beta 1-b and alpha 2), glatiramer acetate or corticosteroids such as methylprednisolone and prednisone. Also, chemotherapeutic agents, such as methotrexate, azathioprine, cladribine, cyclophosphamide and cyclosporine, have been used. All of the above treatments have side-effect liabilities, little or no effect on fatigue and depression, as well as limited effects on relapse rates and on ability to prevent exacerbation of the disease.

Treatment with interferons may also induce the production of neutralizing antibodies, which may ultimately decrease the efficacy of this therapy. Therefore, there still exists a strong need for new drugs, which can be used alone or in combination with other drugs to combat the progression and symptoms of MS.

SUMMARY OF THE INVENTION

The present invention comprises a method of treating multiple sclerosis in patients by administering a compound of Formula I or a pharmaceutically acceptable salt thereof, in a therapeutically effective amount to treat the disease. The present invention also comprises a method of treating multiple sclerosis in patients by administering a combination of a compound of Formula I or a pharmaceutically acceptable salt thereof, with another compound known to be effective for the treatment of multiple sclerosis in therapeutically effective amounts to treat the disease.

In addition, the present invention includes the use of compounds of formula I to treat pain, particularly neuropathic pain and inflammatory pain, especially when such pain is associated with multiple sclerosis.

DETAILED DESCRIPTION OF THE INVENTION

The compounds of formula (I):

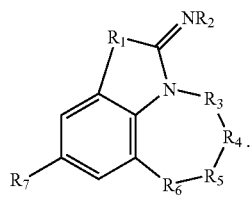

that may be used in the methods of the present invention include their isomers, racemates, enantiomers, and their salts. The invention is also directed to medicaments containing these compounds.

In formula (I), $R_1$ represents a sulphur or selenium atom, $R_2$ represents a hydrogen atom or an alkyl radical, —$R_3$—$R_4$—$R_5$—$R_6$— represents a chain of formula —$CH_2$—$CH_2$—$CH_2$—$CH_2$—, —$CH_2$—$CH_2$—$CH_2$—CO—, —$CH_2$—$CH_2$—$CH_2$—$CH(R_8)$—, —$CH_2$—$CH_2$—$CH_2$—Se—, —$CH_2$—$CH_2$—Se—$CH_2$—, —$CH_2$—$CH_2$—$CH_2$—S—, —$CH_2$—$CH_2$—$CH_2$—SO—, —$CH_2$—$CH_2$—$CH_2$—$SO_2$—, —$CH_2$—$CH_2$—$CH_2$—O—, —$CH_2$—$CH_2$—$CH_2$—$N(R_9)$—, —$CH_2$—$CH_2$—CO—$CH_2$—, —$CH_2$—$CH_2$—$CH(R_8)$—$CH_2$—, —$CH_2$—$CH_2$—S—$CH_2$—, —$CH_2$—$CH_2$—SO—$CH_2$—, —$CH_2$—$CH_2$—$SO_2$—$CH_2$—, —$CH_2$—C(alk)(alk')-S—$CH_2$—, —$CH_2$—C(alk)(alk')-SO—$CH_2$—, —$CH_2$—C(alk)(alk')-$SO_2$—$CH_2$—, —$CH_2$—$CH(R_{10})$—S—$CH_2$—, —$CH_2$—$CH(R_{10})$—SO—$CH_2$—, —$CH_2$—$CH(R_{10})$—$SO_2$—$CH_2$—, —$CH_2$—$CH_2$—O—$CH_2$—, —$CH_2$—$CH_2$—$N(R_9)$—$CH_2$— or —$CH_2$—CO—N$(R_9)$—$CH_2$—, $R_7$ represents a polyfluoroalkyl or polyfluoroalkoxy radical, $R_8$ represents a hydroxyl radical, $R_9$ represents a hydrogen atom or an alkyl or benzyl radical, $R_{10}$ represents an alkyl, —$CH_2OH$, —COOalk, —COOH or —$CONH_2$ radical, alk represents an alkyl radical, alk' represents an alkyl radical.

In the preceding definitions and in those which will be given hereinafter, unless otherwise indicated, the alkyl radicals and portions contain 1 to 6 carbon atoms in straight- or branched-chains.

Among the polyfluoroalkyl radicals, there may be mentioned the trifluoromethyl, 2,2,2-trifluoroethyl, 1,1,2,2-tetrafluoroethyl, perfluoroethyl, perfluoropropyl and perfluorobutyl radicals.

Among the polyfluoroalkoxy radicals, there may be mentioned the trifluoromethoxy, perfluoroethoxy, 2,2,2-trifluoroethoxy, 1,1,2,2-tetrafluoroethoxy, 2,2,3,3,3-pentafluoropropoxy, perfluoropropoxy and perfluorobutoxy radicals.

The preferred polyfluoroalkyl and polyfluoroalkoxy radicals are trifluorbmethyl, trifluoromethoxy and pentafluoroethoxy radicals.

The invention also relates to the addition salts of the compounds of formula (I) with inorganic or organic acids.

The compounds of formula (I) which contain one or more asymmetric centers have isomeric forms; these isomers and mixtures form part of the invention. The racemates and the enantiomers of these compounds also form part of the invention.

Terms used herein have the meanings defined in this specification.

a) "Pharmaceutically acceptable salts" means either an acid addition salt or a basic addition salt, whichever is possible to make with the compounds of the present invention.

"Pharmaceutically acceptable acid addition salt" is any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula 1. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection of the appropriate salt may be important so that the ester is not hydrolyzed. The selection criteria for the appropriate salt will be known to one skilled in the art.

Among the presently preferred salts are the mesylates, hydrochlorides, sulfates and phosphates.

b) "Patients" means warm blooded animals, such as, for example, rats, mice, dogs, cats, guinea pigs, and primates, such as humans.

c) "Treat" or "treating" means any treatment, including, but not limited to, alleviating symptoms, eliminating the causation of the symptoms either on a temporary or permanent basis, or preventing or slowing the appearance of symptoms and progression of the named disorder or condition.

d) "Therapeutically effective amount" means an amount of the compound, which is effective in treating the named disorder or condition.

e) "Pharmaceutically acceptable carrier" is a non-toxic solvent, dispersant, excipient, adjuvant or other material which is mixed with the compound of the present invention in order to permit the formation of a pharmaceutical composition, i.e., a dosage form capable of administration to the patient. One example of such a carrier is a pharmaceutically acceptable oil typically used for parenteral administration.

f) "Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

Synthesis of the compounds of Formula 1 can be accomplished by methods that are well known to those skilled in the art. For example, U.S. Pat. No. 6,369,221, issued on Apr. 9, 2002, discloses suitable methods of synthesis. The contents of the aforementioned patent are hereby incorporated herein by reference.

As disclosed in U.S. Pat. No. 6,369,221, the compounds of formula (I) which contain one or more asymmetric centers have isomeric forms; these isomers and mixtures form part of the invention. The racemates and the enantiomers of these compounds also form part of the invention.

The compounds of formula (I) for which $R_1$ represents a sulphur or selenium atom, $R_2$ represents a hydrogen atom, $-R_3-R_4-R_5-R_6-$ represents a chain of formula $-CH_2-CH_2-CH_2-CH_2-$, $-CH_2-CH_2-CH_2-CO-$, $-CH_2-CH_2-CH_2-CH(R_8)-$, $-CH_2-CH_2-CH_2-Se-$, $-CH_2-CH_2-Se-CH_2-$, $-CH_2-CH_2-CH_2-S-$, $-CH_2-CH_2-CH_2-O-$, $CH_2-CH_2-CH_2-N(R_9)-$, $-CH_2-CH_2-CO-CH_2-$, $-CH_2-CH_2-CH(R_8)-CH_2-$, $-CH_2-CH_2-S-CH_2-$, $-CH_2-C(alk)(alk')-S-CH_2-$, $-CH_2-CH(R_{10})-S-CH_2-$, $-CH_2-CH_2-O-CH_2-$, $-CH_2-CH_2-N(R_9)-CH_2-$ or $-CH_2-CO-N(R_9)-CH_2-$, $R_8$ represents a hydroxyl radical, $R_9$ represents a hydrogen atom or an alkyl or benzyl radical and $R_{10}$ represents an alkyl, COOalk or CONH$_2$ radical,
may be prepared by reacting an alkali metal thiocyanate or an alkali metal selenocyanate with a derivative of formula (II):

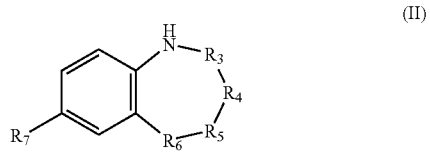

(II)

in which $R_7$ has the same meanings as in formula (I) and $-R_3-R_4-R_5-R_6-$ represents a chain of formula $-CH_2-CH_2-CH_2-CH_2-$, $-CH_2-CH_2-CH_2-CO-$, $-CH_2-CH_2-CH_2-CH(R_8)-$, $-CH_2-CH_2-CH_2-Se-$, $-CH_2-CH_2-Se-CH_2-$, $-CH_2-CH_2-CH_2-S-$, $-CH_2-CH_2-CH_2-O-$, $CH_2-CH_2-CH_2-N(R_9)-$, $-CH_2-CH_2-CO-CH_2-$, $-CH_2-CH_2-CH(R_8)-CH_2-$, $-CH_2-CH_2-S-CH_2-$, $-CH_2-C(alk)(alk')-S-CH_2-$, $-CH_2-CH(R_{10})-S-CH_2-$, $-CH_2-CH_2-O-CH_2-$, $-CH_2-CH_2-N(R_9)-CH_2-$ or $-CH_2-CO-N(R_9)-CH_2-$, $R_8$ represents a hydroxyl radical, $R_9$ represents a hydrogen atom or an alkyl or benzyl radical and $R_{10}$ represents an alkyl, COOalk or CONH$_2$ radical, alk and alk' represent an alkyl radical.

This reaction is generally carried out in the presence of bromine, chlorine, chloramide or copper(II) chloride, in an organic solvent such as acetic acid, at a temperature between 15 degrees C. and the boiling point of the reaction medium. As alkali metal thiocyanate or alkali metal selenocyanate, it is preferable to use potassium thiocyanate or potassium selenocyanate.

The compounds of formula (I) for which $R_2$ represents an alkyl radical may be prepared by alkylation of a corresponding compound of formula (I) for which $R_2$ represents a hydrogen atom.

This alkylation is carried out by any method which makes it possible to alkylate an imine functional group. Preferably, the procedure is carried out by means of a derivative Ra-X in which Ra represents an alkyl radical and X represents a reactive group such as a halogen atom (preferably chlorine, bromine or iodine) or a tosyloxy radical, in an inert organic solvent such as an aliphatic alcohol (1–6C) (ethanol, propanol or butanol for example), a ketone (acetone or methyl ethyl ketone, for example) or dimethylformamide, in the presence of a base such as an alkali metal carbonate (potassium carbonate, for example), at a temperature between 20 degrees C. and the boiling point of the reaction medium.

The compounds of formula (I) for which $R_2$ represents a hydrogen atom or an alkyl radical, $-R_3-R_4-R_5-R_6-$ represents a chain of formula $-CH_2-CH_2-CH(R_8)-CH_2-$ or $-CH_2-CH_2-CH_2-CH(R_8)-$ and $R_8$ represents a hydroxyl radical may also be obtained by reducing a corresponding compound of formula (I), for which $R_2$ represents a hydrogen atom or an alkyl radical and $-R_3-R_4-R_5-R_6-$ represents a chain of formula $-CH_2-CH_2-CO-CH_2-$ or $-CH_2-CH_2-CH_2-CO-$.

This reaction is carried out by any method which makes it possible to convert from a ketone to an alcohol. The procedure is generally carried out by means of sodium borohydride, in an alcohol such as methanol or ethanol, at a temperature of between 0 and 25 degrees C.

The synthesis method described above and in patent application WO99/05147 involves obtaining the methanesulfonate of dioxide-6,6 of 2-imino-9-trifluoromethyl-4,5-dihydro-2H,7H-thiazolo[3,4,5-de][4,1]benzothiazepine in 9 steps from the 4-trifluoromethyl-aniline according to the following reaction scheme (I)

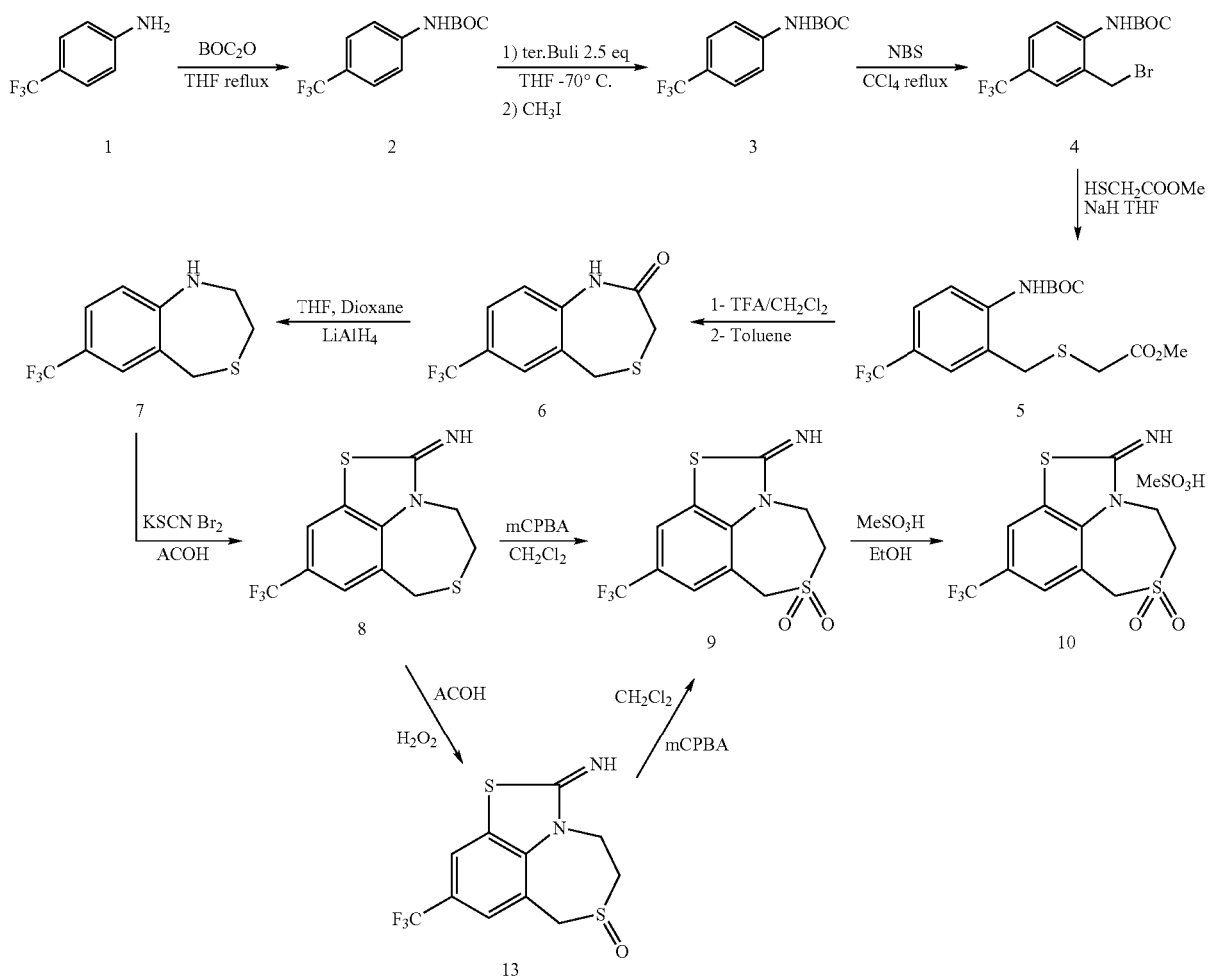

Scheme (I)

In order to obtain the product 2, the product 1 is protected according to standard methods with a BOC group with dicarbonate di tert-butyl in reflux THF. The product 2 is transformed in product 3 with tert butyl lithium, which is highly unstable. In order to obtain the product 4, the methyl function is brominated with N-bromosuccinimide. In order to obtain the intermediate 5, the sulfurated chain is reacted with methyl thioglycolate in the presence of sodium hydride. This intermediate is cyclised in the presence of trifluoroacetic acid. The amide function of the intermediate 6, i.e., 7-trifluoromethyl-1,5-dihydro-3H-[4,1]benzothiazepine-2-one, is reduced to the amine in the presence of lithium tetrahydroaluminate to obtain the intermediate 7, i.e., 7-trifluoromethyl-1,2,3,5-tetrahydro-[4,1]benzothiazepine. The third cycle is added in the presence of potassium and bromine thiocyanate in acetic acid.

The key intermediate 8, i.e., 2-imino-9-trifluoromethyl-4,5-dihydro-2H,7H-thiazolo[3,4,5-de][4,1]benzothiazepine, is thus obtained in 7 steps.

The intermediate 8 is reacted to obtain the final methanesulfonate product, 2-imino-9-trifluoromethyl-4,5-dihydro-2H,7H-thiazolo[3,4,5-de][4,1]benzothiazepine-6,6-dioxide, as well as the corresponding (R,S) 2-imino-9-trifluoromethyl-4,5-dihydro-2H,7H-thiazolo[3,4,5-de][4,1]benzothiazepine-6-oxide as well as its enantiomers.

A recently developed improved synthesis directed to optimizing each of these steps is summarized in reaction scheme (II) below. In particular, this improved synthesis reduces the number of synthesis steps and makes use of other synthesis intermediates, as well as industrial reagents. It also allows a one-step cyclization and, at the same time, avoids the need for purification by chromatography.

Scheme II

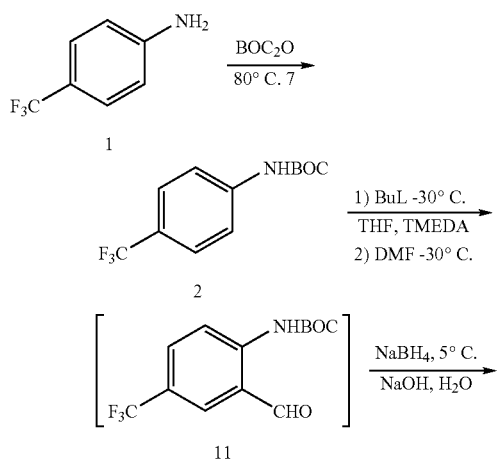

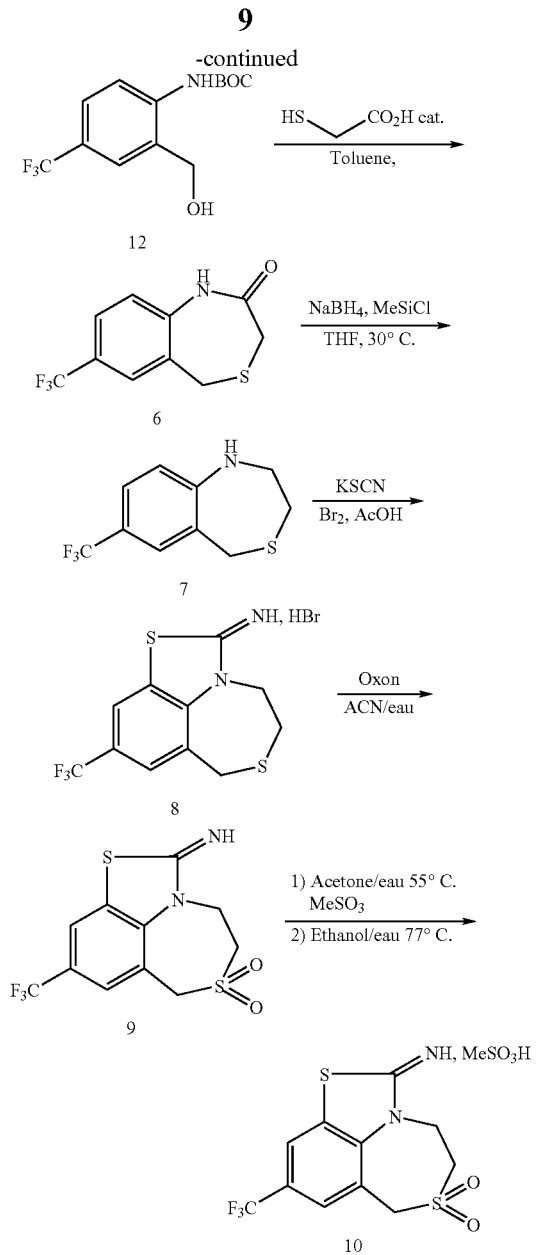

In treating a patient afflicted with a condition described above, a compound of Formula (I) can be administered in any form or mode which makes the compound bioavailable in therapeutically effective amounts, including orally, sublingually, buccally, subcutaneously, intramuscularly, intravenously, transdermally, intranasally, rectally, topically, and the like. One skilled in the art of preparing formulations can determine the proper form and mode of administration depending upon the particular characteristics of the compound selected for the condition or disease to be treated, the stage of the disease, the condition of the patient and other relevant circumstances. For example, see Remington's Pharmaceutical Sciences, 18th Edition, Mack Publishing Co. (1990), the contents of which are hereby incorporated herein by reference.

The compositions of the present invention may be administered orally, for example, in the form of tablets, troches, capsules, elixirs, solutions, suspensions, syrups, wafers, chewing gums and the like and may contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials, which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors.

The compounds of Formula I of this invention may also be administered topically, and, when so done, the carrier may suitably comprise a solution, ointment or gel base. The base, for example, may comprise one or more of petrolatum, lanolin, polyethylene glycols, bee wax, mineral oil, diluents such as water and alcohol, and emulsifiers and stabilizers.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials.

The dosage range at which compounds of Formula I exhibit their ability to act therapeutically can vary depending upon the particular compound, the severity of the condition, the patient, the formulation, other underlying disease states that the patient is suffering from, and other medications that may be concurrently administered to the patient. Generally, the compounds of Formula I will exhibit their therapeutic activities at dosages of between about 0.001 mg/kg of patient body weight/day to about 100 mg/kg of patient body weight/day.

The contents of all publications and patents discussed herein are hereby incorporated herein by reference.

DESCRIPTION OF THE FIGURES

FIG. 1 shows the effect of Compound A, (R,S)-2-imino-9-trifluoromethyl-4,5-dihydro-2H,7H-thiazolo[3,4,5-de][4,1]benzothiazepine-6-oxide, on neurological scores in the Experimental Allergic Encephalomyelitis (EAE) of female SJL mice at doses of 5, 10 and 20 mg/kg when administered orally (p.o.) as compared to vehicle and dexamethasone.

FIG. 2 shows the effect of Compound A, (R,S)-2-imino-9-trifluoromethyl-4,5-dihydro-2H,7H-thiazolo[3,4,5-de][4,1]benzothiazepine-6-oxide, on neurological scores in the Experimental Allergic Encephalomyelitis (EAE) of female SJL mice in a separate experiment at doses of 10, 20 and 30/40 mg/kg.

FIG. 3 shows the effect of Compound A, (R,S)-2-imino-9-trifluoromethyl-4,5-dihydro-2H,7H-thiazolo[3,4,5-de][4,1]benzothiazepine-6-oxide, on neurological scores in the Experimental Allergic Encephalomyelitis (EAE) of female DA (Dark Agouti) rats at doses of 1, 3 and 10 mg/kg when administered orally (p.o.) as compared to vehicle and dexamethasone.

FIG. 4 shows the effect of Compound B, (R,S)-2-imino-9-trifluoromethyl-4,5-dihydro-2H,7H-thiazolo[3,4,5-de][4, 1]benzothiazepine-6,6-dioxide, on neurological scores in the Experimental Allergic Encephalomyelitis (EAE) of female DA rats at doses of 1, 3 and 10 mg/kg when administered orally (p.o.) as compared to vehicle and dexamethasone.

The following examples are being presented to further illustrate the invention. However, they should not be construed as limiting the invention in any manner.

EXAMPLE 1

Effects of Thiazolobenzoheterocyclic Compounds in SJL/J Mouse EAE, an Animal Model of Multiple Sclerosis.

The utility of the thiazobenzohetercyclic compounds of formula I for the treatment of various conditions associated with multiple sclerosis can be assessed by measuring their ability to inhibit effects of experimental allergic encephalomyelitis (EAE) in laboratory animals.

Experimental Autoimmune Encephalomyelitis (EAE) is a T-cell-mediated autoimmune disease of the nervous system that develops in susceptible animals following sensitization with either whole spinal cord homogenate or a myelin component. It is known that EAE reflects or mimics many of the pathophysiological steps in MS, including the role of certain adhesion molecules, the influence of T cells and antibodies reactive to components of the myelin sheath, the participation of metalloproteases in penetrating the blood-brain barrier, and the cytotoxic role of certain cytokines. One of the marketed MS therapies, glatiramer acetate (Copaxone®) was developed preclinically based on its success in treating various models of EAE.

EAE was induced in female SJL/J mice (8 wks old, from Jackson Laboratories) by immunization with the myelin Proteolipid Protein (PLP 139–151) from BACHEM, Bioscience. PLP139–151 was dissolved in $H_2O:PBS$ (1:1) solution to a concentration of 7.5 mg/10 ml (for 75 ug PLP per mouse) and emulsified with an equal volume of CFA supplemented with 40 mg/10 ml heated-killed mycobacterium tuberculosis H37Ra (BD Bioscience). Mice were injected s.c. with 0.2 ml of peptide emulsion in the abdominal flank (0.1 ml on each side). On the same day and 72 hr later, mice were injected i.v. with 35 ng and 50 ng of Bordetella Pertussis toxin (List Biological Laboratories ) in saline, respectively.

Mice were scored daily before treatment starting from day 7 post-immunization through the entire experiment by a well-known behavioral scale system: Score 0, normal; 0.5, partial limp tail; 1, complete limp tail; 2, impaired righting reflex; 2.5, significantly impaired righting reflex and notable weakness in hind limbs; 3, partial hind limb paralysis, and mice unable to walk normally; 3.5, one leg is completely paralyzed, and one leg is partially paralyzed; 4, complete hind limb paralysis; 4.5, Legs are completely paralyzed and Moribund; 5, death due to EAE. Compound A, one representative of thiazolobenzoheterocyclic compounds, was examined in the PLP/SJL mouse EAE model.

Study 1: There were five groups, i.e., vehicle (water), Compound A at doses of 5, 10 and 20 mg/kg and dexamethasone (DEX) at a dose of 3 mg/kg. Treatment was begun on day 7 after PLP immunization. Mice were dosed twice per day for 22 days. Results are as follows:

As seen in FIG. 1, Compound A at doses of 10 and 20 mg/kg significantly reduced neurological deficits in the EAE mice Study 2: There were five groups, i.e., vehicle (water), Compound A at doses of 10, 20 and 30/40 mg/kg and dexamethasone (DEX) at a dose of 3 mg/kg. Treatment was begun on day 7 after PLP immunization. Mice were dosed twice per day for 18 days. Results are as fellows:

At doses of 10 and 20 mg/kg, Compound A significant reduced neurological scores in SJL EAE mice. Further analyses shows that Compound A also reduced EAE incidence and delayed disease onset.

EXAMPLE 2

Effects of Thiazolobenzoheterocyclic Compounds in DA Rat EAE

EAE was induced in female DA (Dark Agouti) rats (8 wks old, from Harlan) by immunization with the 25% w/v rat spinal cord homogenate (r-SCH) in saline emulsified with an equal volume of CFA supplemented with 40 mg/10 ml heated-killed mycobacterium tuberculosis H37Ra (BD Bioscience). Rats were injected s.c. with 0.2 ml of emulsion in the base of tail.

Rats were scored daily before treatment starting from day 5 post-immunization through the entire experiment by a well-known behavioral scale system: Score 0, normal; 0.5, partial limp tail; 1, complete limp tail; 2, abnormal gait; 3, partial hind limb paralysis, and mice unable to walk normally; 3.5, one leg is completely paralyzed, and one leg is partially paralyzed; 4, complete hind limb paralysis; 4.5, Legs are completely paralyzed and Moribund; 5, death due to EAE. Compound A and Compound B (active metabolite of Compound A), two representatives of thiazolobenzoheterocyclic compounds, were examined in DA rat EAE procedure.

Compound A and Compound B were given one-day post-immunization, p.o. route, twice daily for 28 days. Results are as fellows:

At doses of 1, 3 and 10 mg/kg, both Compounds A and B significantly reduced EAE incidence, maximal and cumulative neurological scores.

What is claimed is:

1. A method of treating multiple sclerosis which comprises administering to a patient having multiple sclerosis a therapeutically effective amount of a compound of Formula I,

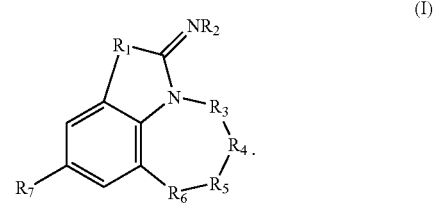

in which $R_1$ is a sulphur or selenium atom, $R_2$ is a hydrogen atom or an alkyl radical, —$R_3$—$R_4$—$R_5$—$R_6$— is a chain of formula —$CH_2$—$CH_2$—$CH_2$—$CH_2$—, —$CH_2$—$CH_2$—$CH_2$—CO—, —$CH_2$—$CH_2$—$CH_2$—$CH(R_8)$—, —$CH_2$—$CH_2$—$CH_2$—Se—, —$CH_2$—$CH_2$—Se—$CH_2$—, —$CH_2$—$CH_2$—$CH_2$—S—, —$CH_2$—$CH_2$—$CH_2$—SO—, —$CH_2$—$CH_2$—$CH_2$—$SO_2$—, —$CH_2$—$CH_2$—$CH_2$—O—, —$CH_2$—$CH_2$—$CH_2$—$N(R_9)$—, —$CH_2$—$CH_2$—CO—$CH_2$—, —$CH_2$—$CH_2$—$CH(R_8)$—$CH_2$—, —$CH_2$—$CH_2$—S—$CH_2$—, —$CH_2$—$CH_2$—SO—$CH_2$—, —$CH_2$—$CH_2$—$SO_2$—$CH_2$—, —$CH_2$—C(alk)(alk')—S—$CH_2$—, —$CH_2$—C(alk)(alk')—SO—$CH_2$—, —$CH_2$—C(alk)(alk')—$SO_2$—$CH_2$—, —$CH_2$—$CH(R_{10})$—S—$CH_2$—, —$CH_2$—$CH(R_{10})$—SO—$CH_2$—, —$CH_2$—$CH(R_{10})$—$SO_2$—$CH_2$—, —$CH_2$—$CH_2$—O—$CH_2$—, —$CH_2$—$CH_2$—$N(R_9)$—$CH_2$— or —$CH_2$—CO—$N(R_9)$—$CH_2$—, R₇ is a polyfluoroalkyl or polyfluoroalkoxy radical, R₈ is a hydroxyl radical, R₉ is a hydrogen atom or an alkyl or benzyl radical, R₁₀ is an alkyl, —CH₂OH, —COOalk, —COOH or —CONH₂ radical, alk is an alkyl radical, alk' is an alkyl radical, the alkyl radicals containing 1 to 6 straight- or branched-chain carbon atoms, and, when said compound contains one or more asymmetric centers, its isomers, racemates and enantiomers, and the salts of said compound with an inorganic or organic acid.

2. The method of claim 1 wherein, in said compound of formula 1, R₇ is a trifluoromethoxy or trifluoromethyl radical.

3. The method of claim 1 wherein, in said compound of formula 1, R₁ is a sulphur atom, R₂ is a hydrogen atom, —R₃—R₄—R₅—R₆— is a chain of formula —CH₂—CH₂—CH₂—CH₂—, —CH₂—CH₂—CH₂—CO—, —CH₂—CH₂—CH₂—CH(R₈)—, —CH₂—CH₂—CH₂—Se—, —CH₂—CH₂—Se—CH₂—, —CH₂—CH₂—CH₂—S—, —CH₂—CH₂—CH₂—SO—, —CH₂—CH₂—CH₂—SO₂—, —CH₂—CH₂—CH₂—O—, —CH₂—CH₂—CH₂—N(R₉)—, —CH₂—CH₂—CO—CH₂—, —CH₂—CH₂—CH(R₈)—CH₂—, —CH₂—CH₂—S—CH₂—, —CH₂—CH₂—SO—CH₂—, —CH₂—CH₂—SO₂—CH₂—, —CH₂—C(alk)(alk')—S—CH₂—, —CH₂—C(alk)(alk')—SO—CH₂—, —CH₂—C(alk)(alk')—SO₂—CH₂—, —CH₂—CH(R₁₀)—S—CH₂—, —CH₂—CH(R₁₀)—SO—CH₂—, —CH₂—CH(R₁₀)—SO₂—CH₂—, —CH₂—CH₂—O—CH₂—, —CH₂—CH₂—N(R₉)—CH₂— or —CH₂—CO—N(R₉)—CH₂—, R₇ is a trifluoromethyl or trifluoromethoxy radical, R₈ is a hydroxyl radical, R₉ is a hydrogen atom or an alkyl or benzyl radical, R₁₀ is an alkyl, —CH₂OH, —COOalk, —COOH or —CONH₂ radical, alk is an alkyl radical and alk' is an alkyl radical.

4. The method of claim 1 wherein, said compound of formula 1 is selected from the group consisting of:

2-imino-9-trifluoromethoxy-4,5,6,7-tetrahydro-2H-thiazolo[5,4,3-jk][1]benzazepin-7-ol, 2-imino-9-trifluoromethoxy-4,5,6,7-tetrahydro-2H-thiazolo[5,4,3-jk][1]benzazepine, 2-imino-9-trifluoromethyl-4,5,6,7-tetrahydro-2H-thiazolo[5,4,3-jk][1]benzazepine, 2-imino-9-trifluoromethoxy-5,6-dihydro-2H,4H-thiazolo[3,4,5-ef][1,5]benzothiazepine 7,7-dioxide, 2-imino-9-trifluoromethoxy-5,6-dihydro-2H,4H-thiazolo[3,4,5-ef][1,5]benzothiazepine 7-oxide, 2-imino-9-trifluoromethoxy-5,6-dihydro-2H,4H-thiazolo[3,4,5-ef][1,5]benzothiazepine, 6-benzyl-2-imino-9-trifluoromethoxy-6,7-dihydro-4H-thiazolo[3,4,5-kj][1,4]benzodiazepin-5-one, 6-benzyl-2-imino-9-trifluoromethoxy-4,5,6,7-tetrahydro-2H-thiazolo[3,4,5-kj][1,4]benzodiazepine, 2-imino-9-trifluoromethoxy-4,5-dihydro-2H,7H-thiazolo[3,4,5-de][4,1]benzothiazepine, 2-imino-9-trifluoromethyl-4,5-dihydro-2H,7H-thiazolo[3,4,5-de][4,1]benzothiazepine, 2-imino-9-trifluoromethyl-4,5-dihydro-2H,7H-thiazolo[3,4,5-de][4,1]benzothiazepine 6,6-dioxide, 2-imino-9-trifluoromethyl-5,6-dihydro-2H,4H-thiazolo[3,4,5-ef][1,5]benzothiazepine 7-oxide, 2-imino-9-trifluoromethyl-5,6-dihydro-2H,4H-thiazolo[3,4,5-ef][1,5]benzothiazepine 6,6-dioxide, 2-imino-9-trifluoromethyl-5,6-dihydro-2H,4H-thiazolo[3,4,5-ef][1,5]benzothiazepine, 2-imino-9-trifluoromethyl-4,5,6,7-tetrahydro-2H-thiazolo[5,4,3-jk][1]benzazepin-7-ol, 2-imino-9-trifluoromethoxy-4,5-dihydro-2H,7H-thiazolo[3,4,5-de][4,1]benzothiazepine 6,6-dioxide, 2-imino-9-trifluoromethoxy-4,5-dihydro-2H,7H-thiazolo[3,4,5-de][4,1]benzothiazepine 6-oxide, 6-benzyl-2-imino-9-trifluoromethyl-6,7-dihydro-4H-thiazolo[3,4,5-kj][1,4]benzodiazepin-5-one, 6-benzyl-2-imino-9-trifluoromethyl-4,5,6,7-tetrahydro-2H-thiazolo[3,4,5-kj][1,4]benzodiazepine, 2-imino-5-methyl-9-trifluoromethyl-4,5-dihydro-2H,7H-thiazolo[3,4,5-de][4,1]benzothiazepine, 5-carbamoyl-2-imino-9-trifluoromethyl-4,5-dihydro-2H,7H-thiazolo[3,4,5-de][4,1]benzothiazepine, 5,5-dimethyl-2-imino-9-trifluoromethyl-2H,4H,7H-thiazolo[3,4,5-de][4,1]benzothiazepine, 5-hydroxymethyl-2-imino-9-trifluoromethyl-4,5-dihydro-2H,7H-thiazolo[3,4,5-de][4,1]benzothiazepine, and, when they contain one or more asymmetric centres, their isomers, racemates, enantiomers and their salts with an inorganic or organic acid.

5. The method of claim 1 wherein, said compound of formula 1 is selected from the group consisting of:

(R,S)-2-imino-9-trifluoromethyl-4,5-dihydro-2H,7H-thiazolo[3,4,5-de][4,1]benzothiazepine-6-oxide, (+)-2-imino-9-trifluoromethyl-4,5-dihydro-2H,7H-thiazolo[3,4,5-de][4,1]benzothiazepine-6-oxide, (−)-2-imino-9-trifluoromethyl-4,5-dihydro-2H,7H-thiazolo[3,4,5-de][4,1]benzothiazepine-6-oxide, (R,S)-2-imino-5-methyl-9-trifluoromethyl-4,5-dihydro-2H,7H-thiazolo[3,4,5-de][4,1]benzothiazepine-6,6-dioxide, (+)-2-imino-5-methyl-9-trifluoromethyl-4,5-dihydro-2H,7H-thiazolo[3,4,5-de][4,1]benzothiazepine-6,6-dioxide, (−)-2-imino-5-methyl-9-trifluoromethyl-4,5-dihydro-2H,7H-thiazolo[3,4,5-de][4,1]benzothiazepine-6,6-dioxide, and their salts with an inorganic or organic acid.

6. A method of treating inflammatory or neuropathic pain comprising administering to a patient in need thereof an effective amount of a compound of formula I as defined in claim 1.

7. The method of claim 6 wherein said pain is associated with multiple sclerosis.

* * * * *